United States Patent
Gofman et al.

(10) Patent No.: US 8,247,233 B2
(45) Date of Patent: Aug. 21, 2012

(54) INTEGRATED FLUID ANALYTE METER SYSTEM

(75) Inventors: Igor Gofman, Croton-on-Hudson, NY (US); Mitchel Stein, Cortlandt Manor, NY (US)

(73) Assignee: Bayer Healthcare LLC, Tarrytown, NY (US)

(*) Notice: Subject to any disclaimer, the term of this patent is extended or adjusted under 35 U.S.C. 154(b) by 852 days.

(21) Appl. No.: 12/316,116

(22) Filed: Dec. 9, 2008

(65) Prior Publication Data
US 2009/0149725 A1    Jun. 11, 2009

Related U.S. Application Data

(60) Provisional application No. 61/007,086, filed on Dec. 10, 2007.

(51) Int. Cl.
*G01N 35/02* (2006.01)
*G01N 35/00* (2006.01)
*G01N 21/75* (2006.01)
*G01J 1/48* (2006.01)

(52) U.S. Cl. ............ 436/48; 422/50; 422/68.1; 422/87; 422/400; 422/402; 422/403; 422/410; 422/412; 422/417; 422/430; 422/554; 436/14; 436/46; 436/95; 600/583; 600/584

(58) Field of Classification Search .......... 422/50, 422/68.1, 410, 417, 87, 400, 402, 403, 412, 422/430, 554; 436/44, 95, 14, 46, 48; 600/300, 600/583, 584
See application file for complete search history.

(56) References Cited

U.S. PATENT DOCUMENTS 7,922,971 B2 * 4/2011 Bryer et al. ............ 422/50
2007/0123803 A1   5/2007 Fujiwara et al.

FOREIGN PATENT DOCUMENTS

| DE | 198 11 622 | * | 9/1999 |
| EP | 1 360 935 | * | 5/2003 |
| EP | 1 360 932 |   | 11/2003 |
| EP | 1 360 935 |   | 11/2003 |
| WO | WO 2005/107596 |   | 11/2005 |
| WO | WO 2008/043565 |   | 4/2008 |

OTHER PUBLICATIONS

PCT Search Report for International Application No. PCT/US2008/085772 dated Mar. 30, 2009 (6 pages).
PCT Written Opinion for International Application No. PCT/US2008/085772 dated Mar. 30, 2009 (7 pages).

* cited by examiner

*Primary Examiner* — Gail R Gabel
(74) *Attorney, Agent, or Firm* — Nixon Peabody LLP

(57) ABSTRACT

An integrated meter system for determining information related to an analyte of a fluid sample includes a meter including a housing and a plurality of test sensors. Each of the plurality of test sensors includes a penetrating member, a testing portion, and a channel. The channel is adapted to receive the fluid sample. The test sensors are removably located within the housing. At least one of the test sensors is removably connected to an adjacent test sensor. The integrated meter system also includes a test-sensor advancement mechanism that is configured to advance the test sensors.

20 Claims, 8 Drawing Sheets

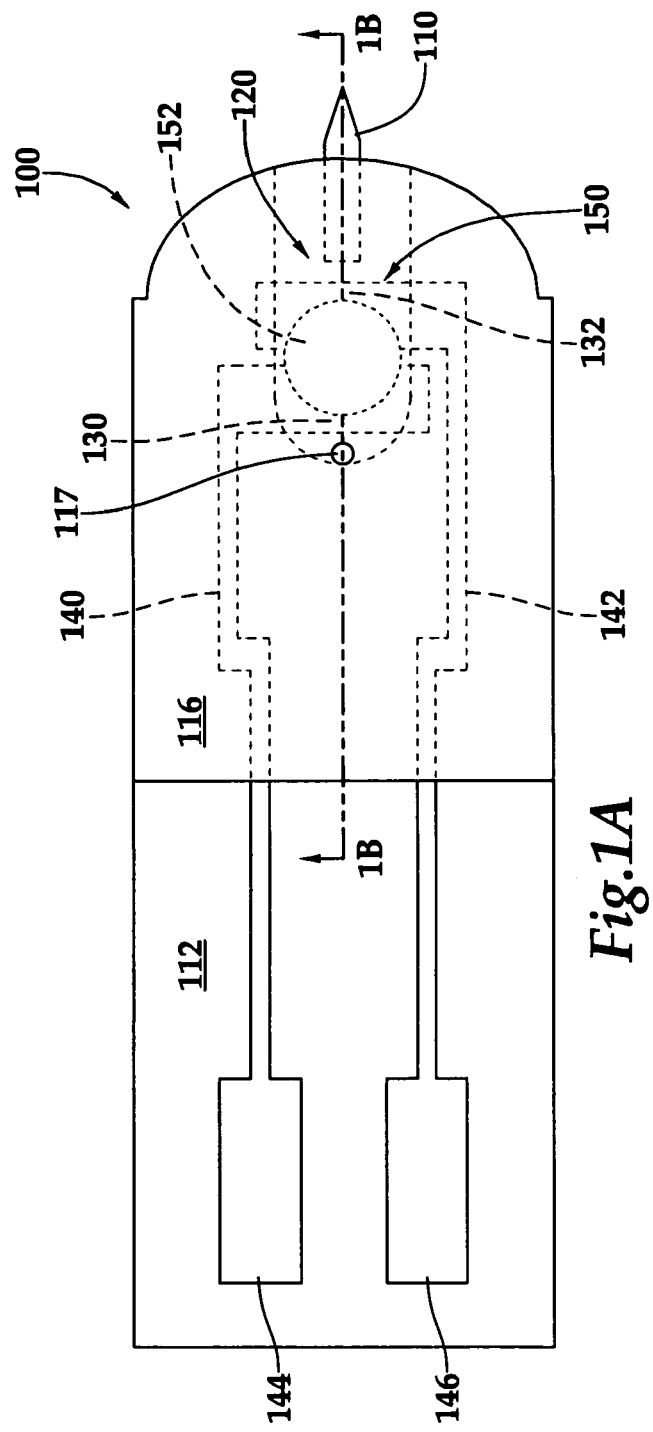
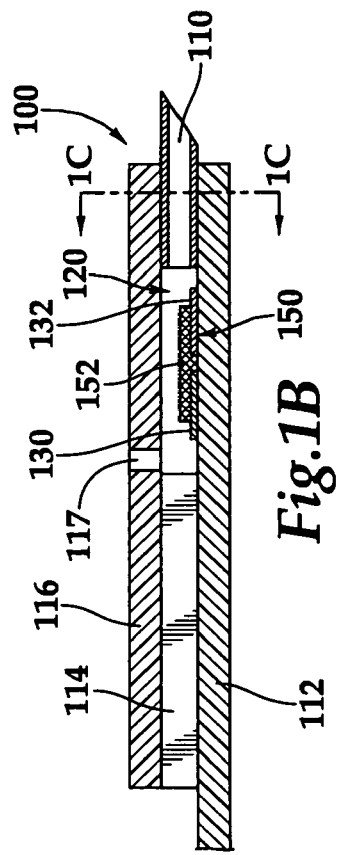
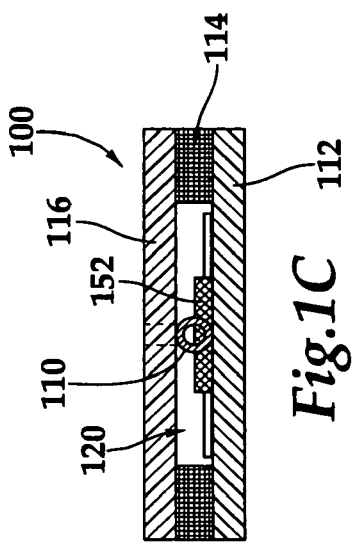
Fig.1A
Fig.1B
Fig.1C

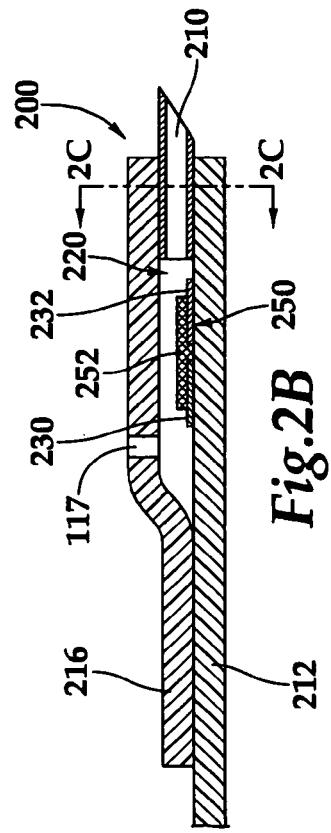
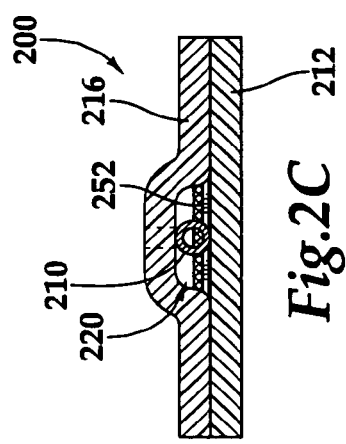
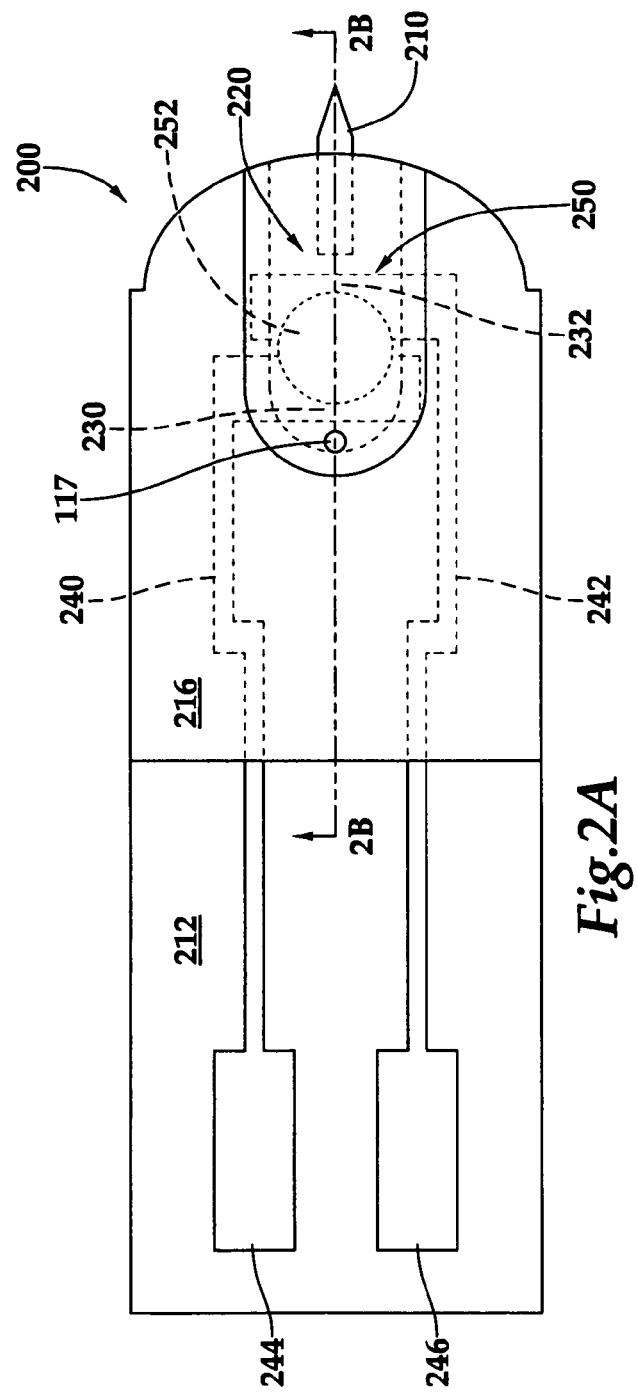

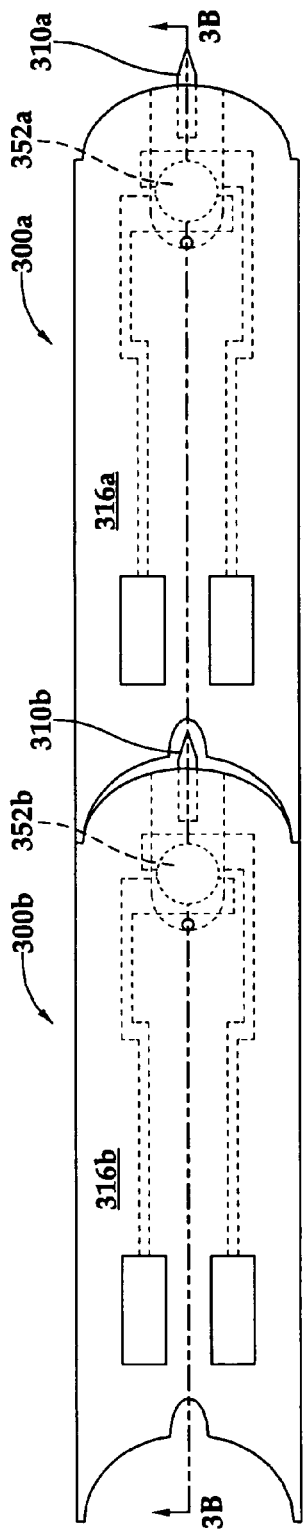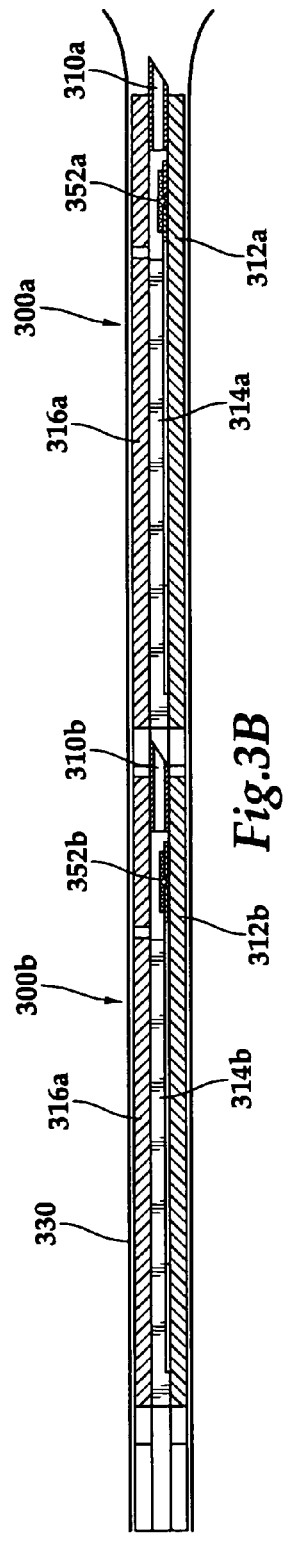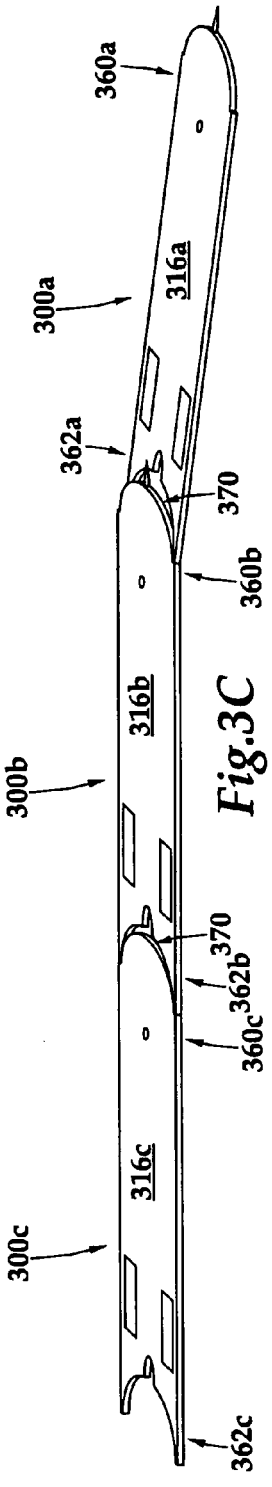

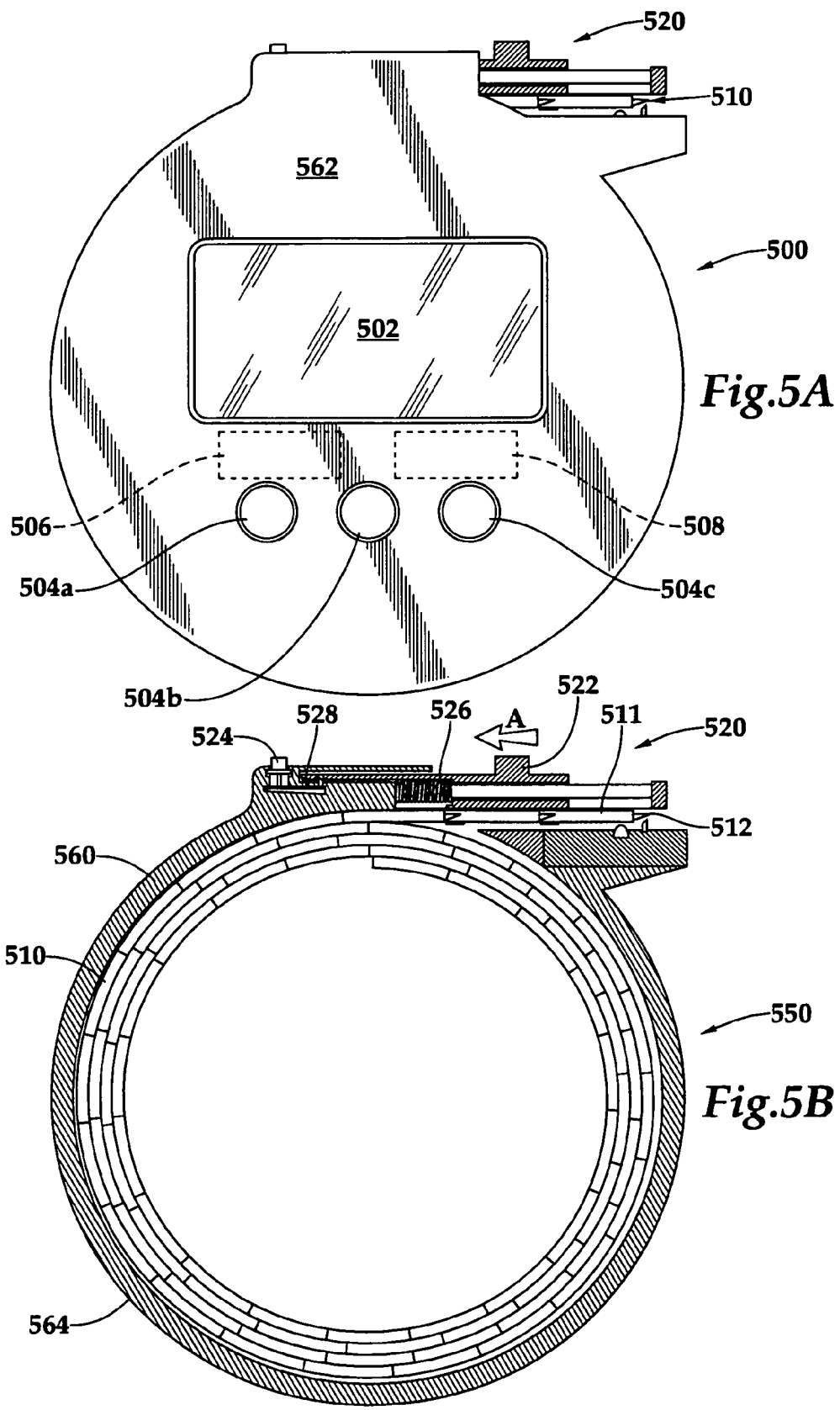

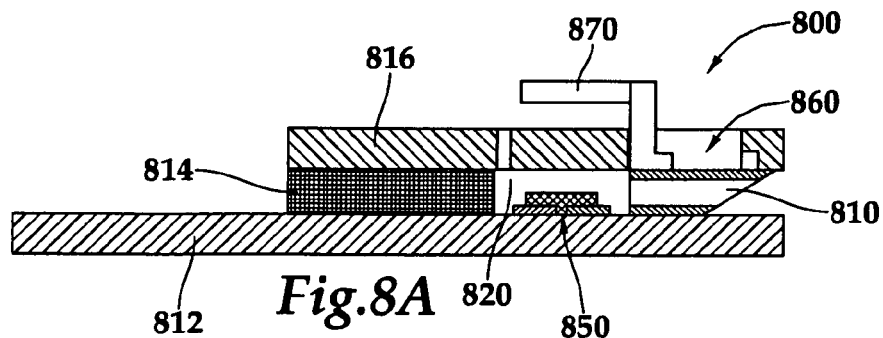
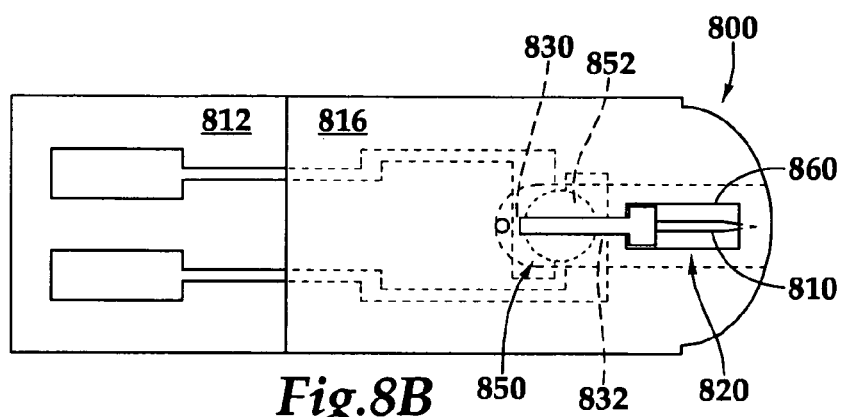
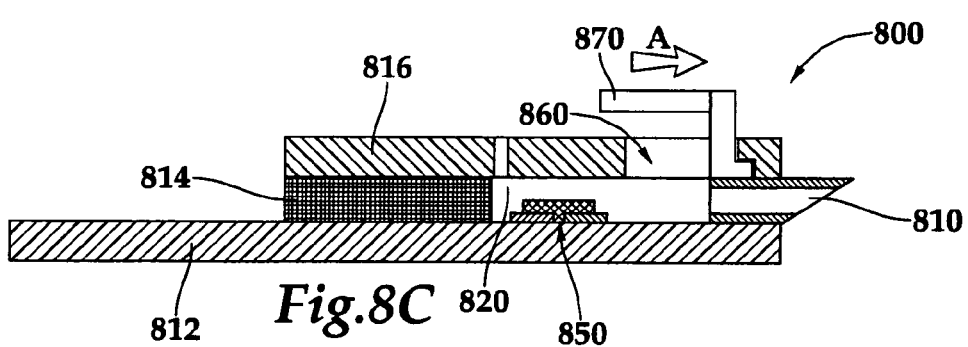
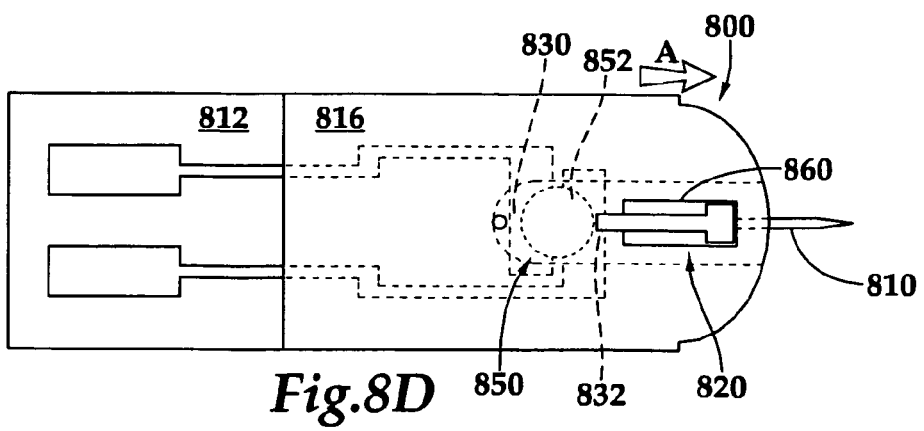

INTEGRATED FLUID ANALYTE METER SYSTEM

CROSS REFERENCE TO RELATED APPLICATIONS

This application claims priority to U.S. Provisional Application No. 61/007,086, filed Dec. 10, 2007, the contents of which are incorporated entirely herein by reference.

FIELD OF THE INVENTION

The present invention relates generally to an integrated meter system for determining information related to an analyte of a fluid sample and methods of using the same. More specifically, the present invention relates to an integrated meter system including a meter and a test sensor including a penetrating member.

BACKGROUND OF THE INVENTION

The quantitative determination of analytes in body fluids is of great importance in the diagnoses and maintenance of certain physical conditions. For example, blood glucose, hemoglobin (Hb), hemoglobin $Al_c$ ($HbAl_c$), lactate, cholesterol, bilirubin, and other analytes should be monitored in certain individuals. In particular, it is important that individuals who have diabetics frequently check the glucose level in their body fluids because such individuals may become ill if their blood glucose level becomes too high—a condition known as hyperglycemia. The results of these analyte tests may be used to determine what, if any, insulin or other medication should be administered.

The analyte concentration tests are typically performed using optical or electrochemical testing methods. In the embodiments employing an electrochemical method, a test sensor contains biosensing or reagent material that reacts with, for example, blood glucose. A testing portion of the test sensor contains the reagent material and is adapted to receive a fluid (e.g., blood) being tested that has accumulated on, for example, a person's finger after the finger has been pricked. The fluid is typically drawn into a channel that extends in the test sensor from a first end near the front of the test sensor to the reagent material, located in the testing portion. In certain embodiments, the test sensor draws the fluid into the channel using capillary action so that a sufficient amount of the fluid to be tested is drawn into the test sensor's testing portion. The fluid then chemically reacts with the reagent material in the testing portion. This results in an electrical signal, indicative of the glucose level in the fluid, being supplied to electrical contact areas, which are located at a second opposing end near the rear or contact portion of the test sensor.

Analyte concentration readings of a fluid sample typically require using a penetrating member or a lancing device in conjunction with a test sensor. In certain embodiments, the meter system integrates the penetrating member with a meter for convenient side-by-side lancing and testing. However, locating the penetrating member and the test sensor in different positions on the meter typically requires multiple steps, added difficulty in operation of the meter, and potentially added bulk to the meter.

It would be desirable to overcome the above-noted shortcoming of existing systems, while providing a simple, easy, and single-handed operable meter system for determining information related to an analyte of a fluid sample.

SUMMARY OF THE INVENTION

According to one embodiment, an integrated meter system for determining information related to an analyte of a fluid sample includes a meter including a housing and a plurality of test sensors. Each of the plurality of test sensors includes a penetrating member, a testing portion, and a channel. The channel is adapted to receive the fluid sample. The plurality of test sensors is removably located within the housing. At least one of the plurality of test sensors is removably connected to an adjacent test sensor. The integrated meter system also includes a test-sensor advancement mechanism that is configured to advance the plurality of test sensors.

According to another embodiment, a method of forming a test-sensor system adapted to assist in determining information related to an analyte of a fluid sample includes providing a plurality of test sensors. Each of the plurality of test sensors includes a base, and a second layer attached to the base. The base and the attached second layer assist in forming a channel to receive the fluid sample. Reagent material is located within the channel. A penetrating member is attached to the base or the second layer. The method further includes attaching a sealing tape to a surface of each of the plurality of test sensors to assist in preventing or inhibiting communication between the reagent material and the atmosphere.

According to another embodiment, a method of using an integrated meter system for determining information related to an analyte of a fluid sample includes providing a meter with a housing. The method further includes providing a plurality of test sensors. At least one of the plurality of test sensors is removably connected to an adjacent test sensor. Each one of the plurality of test sensors includes a penetrating member, a testing portion, and a channel. The channel is adapted to receive the fluid sample and is further in communication with the testing portion. The plurality of test sensors is located within the housing. The method further includes advancing at least one of the plurality of test sensors incrementally and engaging the penetrating member of one of the plurality of test sensors with a portion of a user's skin. The method further includes collecting the fluid sample through the channel to the testing portion and determining the information related to the analyte of the fluid sample.

According to another embodiment, an integrated meter system for determining information related to an analyte of a fluid sample includes a meter with a housing and a plurality of test sensors. Each of the plurality of test sensors includes a lid, a base, a penetrating member, a testing portion, and a channel. The channel is adapted to receive the fluid sample. The plurality of test sensors is removably located within the housing. At least one of the plurality of test sensors is removably connected to an adjacent test sensor. A sealing member is removably connected to at least one of the respective lids and/or bases of the plurality of test sensors. The integrated meter system further includes a test-sensor advancement mechanism that is configured to advance the plurality of test sensors.

BRIEF DESCRIPTION OF THE DRAWINGS

FIG. 1a is top view of a test sensor according to one embodiment of the present invention.

FIG. 1b is a cross-sectional side view of the test sensor of FIG. 1a taken generally along line 1B-1B of FIG. 1a.

FIG. 1c is a cross-sectional view of the test sensor of FIG. 1b taken generally along line 1C-1C of FIG. 1B.

FIG. 2a is a top view of a test sensor according to another embodiment of the present invention.

FIG. 2b is a cross-sectional side view of the test sensor of FIG. 2a taken generally along line 2B-2B of FIG. 2A.

FIG. 2c is a cross-sectional view of the test sensor shown of FIG. 2b taken generally along line 2C-2C of FIG. 2B.

FIG. 3a is a top view of a plurality of removably connected test sensors according to one embodiment of the present invention.

FIG. 3b is a cross-sectional side view of the plurality of test sensors taken generally along line 3B-3B of FIG. 3A.

FIG. 3c is a perspective view of the plurality of removably connected test sensors of FIG. 3a.

FIG. 5a is a front view of a meter with a display and input mechanism according to one embodiment.

FIG. 5b is a front view of a meter with the housing cut-away in a loaded position according to one embodiment.

FIG. 8a is a cross-sectional side view of a test sensor-advancement mechanism engaging a test sensor according to one embodiment of the present invention.

FIG. 8b is a top view of the test sensor shown in FIG. 8a.

FIG. 8c is a cross-sectional side view of the test sensor shown in FIG. 8a with the penetrating member extended according to one embodiment.

FIG. 8d is a top view of the test sensor shown in FIG. 8c.

Figure 4A:
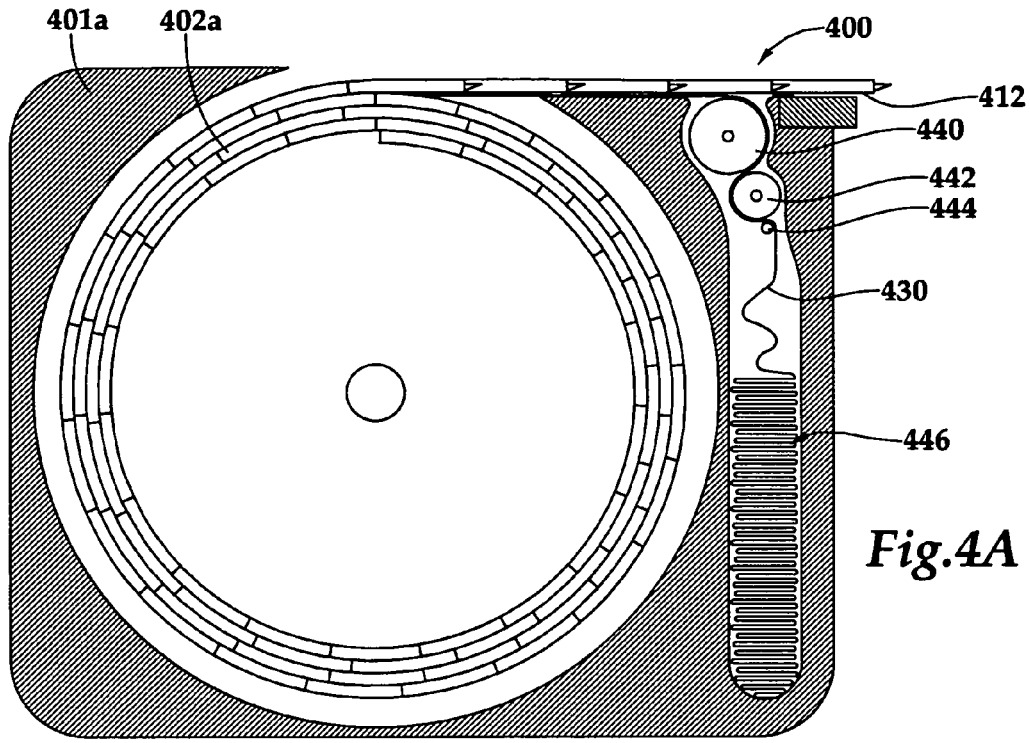
FIG. 4a is a front view of a meter with the housing cut-away according to one embodiment of the present invention.

While the invention is susceptible to various modifications and alternative forms, specific embodiments are shown by way of example in the drawings and are described in detail herein. It should be understood, however, that the invention is not intended to be limited to the particular forms disclosed. Rather, the invention is to cover all modifications, equivalents, and alternatives falling within the spirit and scope of the invention.

DETAILED DESCRIPTION OF ILLUSTRATED EMBODIMENTS

The present invention is directed to an integrated meter system adapted to determine information related to an analyte of a fluid sample (e.g., blood). Specifically, the present invention is directed to an integrated fluid analyte meter system including a meter, a plurality of test sensors, and a penetrating member to assist a user in determining information related to an analyte of a fluid sample taken from a user. A test sensor is typically adapted to receive a fluid sample, which an instrument or meter subsequently analyzes to produce information of an analyte such as a concentration reading. Analytes that may be measured include glucose, lipid profiles (e.g., cholesterol, triglycerides, LDL, and HDL), microalbumin, hemoglobin $A_{1C}$, fructose, lactate, or bilirubin. It is contemplated that other analyte concentrations may be determined. The analytes may be in, for example, a whole blood sample, a blood serum sample, a blood plasma sample, other body fluids like ISF (interstitial fluid), creatinine, urea, urine, and non-body fluids.

The plurality of test sensors may be electrochemical test sensors. The electrochemical test sensors include at least a base, an electrode pattern, a second layer such as a lid and/or a spacer, and a penetrating member. In one embodiment, the electrochemical test sensors include a base, an electrode pattern, a lid, and a penetrating member. In another embodiment, the electrochemical test sensors include a base, an electrode pattern, a spacer, a lid, and a penetrating member.

The base, spacer, and lid may be made from a variety of materials such as polymeric materials. Non-limiting examples of polymeric materials that may be used to form the base, spacer, and lid include polycarbonate, polyethylene terephthalate (PET), polystyrene, polyimide, and combinations thereof. It is contemplated that the base, spacer, and lid may be independently made of other materials. The electrode pattern may be formed from a variety of conductive materials including, but not limited to, carbon, gold, platinum, palladium or combinations thereof.

One non-limiting example of an electrochemical test sensor is shown in FIGS. 1a-c. FIGS. 1a-c depict an electrochemical test sensor 100 that includes a penetrating member 110, a base 112, a spacer 114, and a lid 116. To form the test sensor 100, the base 112, the spacer 114, and the lid 116 are attached by, for example, an adhesive or heat sealing. A channel 120 (e.g., capillary channel) is formed when the base 112, the spacer 114, and the lid 116 are attached to each other. The penetrating member 110 of FIG. 1b is attached to the base 112 and the lid 116 such that a fluid sample introduced into the test sensor 100 may flow through the penetrating member 110 and into the channel 120 and eventually reaching a testing or reactive portion 150. The testing portion 150 includes at least two electrodes and a reagent material 152. The lid 116 may include a vent 117 to assist the flow of the fluid sample into the channel 120.

Referring to FIG. 1a, which is a top view of the test sensor 100, the test sensor 100 includes the testing portion 150 that includes the reagent material 152. The reagent material typically includes an enzyme. The enzyme is selected to react with the desired analyte or analytes to be tested so as to assist in determining information related to an analyte of a fluid sample. The reagent material 152 converts an analyte of interest (e.g., glucose) in a fluid test sample (e.g., blood) into a chemical species that is electrochemically measurable, in terms of the electrical current it produces, by the components of the electrode pattern.

The base 112 includes conductive material and, more specifically, a plurality of electrodes 130 and 132, a plurality of conductive leads or traces 140, 142 and test-sensor contacts 144, 146. The plurality of electrodes of FIG. 1a includes at least a counter electrode 130 and a working electrode 132. The working electrode measures the current when a potential is applied across the working and counter electrodes. The counter electrode should be sufficiently large so as to support the reaction occurring at the working electrode. The applied voltage may be referenced to the reagent deposited adjacent to the counter electrode. It is contemplated that the test sensor 100 may include other electrodes such as a trigger electrode, a detection electrode, a hematocrit electrode, or a second working electrode.

The electrodes are formed of conductive materials such as, for example, metallic materials (e.g., gold, platinum, palladium, rhodium, ruthenium, or combinations thereof) or carbon.

Another non-limiting example of an electrochemical test sensor is shown in FIGS. 2a-c. FIGS. 2a-c depict an electrochemical test sensor 200 that includes a penetrating member 210, a base 212, and a lid 216. The base 212 may be the same or similar to the base 112 discussed above. The lid 216 may be formed with a convex opening that is adapted to receive a fluid sample through the attached penetrating member 210. FIG. 2a depicts the base 212 and a channel 220 (e.g., capillary channel) that is formed when the base 212 and the lid 216 are attached to each other. The penetrating member 210 is attached to the lid 216 such that the fluid sample introduced into the test sensor 200 may flow through the penetrating member 210 and into the channel 220 and eventually reaching a testing portion 250. The testing portion 250 includes at least two electrodes and a reagent material 252.

Referring to FIG. 2a, the electrodes formed on the base 212 may be the same as described above with respect to the base 112. The electrodes include a counter and working electrode 230, 232. The electrodes 230, 232 are electrically connected to two test-sensor contacts 244, 246 via leads or traces 240, 242 for electrically connecting the test sensor 200 to a meter. In other embodiments, the electrodes may include additional electrodes such as the above discussed trigger electrode, detection electrode, hematocrit electrode, a second working electrode and other electrodes.

Test sensors 100 and 200, described in relation to FIGS. 1a-c and 2a-c, include the penetrating members 110 and 210 respectively. The penetrating members 110,210 are used to prick the skin of the user (i.e., break the skin). In the embodiments depicted in FIGS. 1a-c and 2a-c, the fluid (e.g., blood) may be drawn into the channel 120,220 directly through a respective penetrating member 110,210, where the penetrating members 110,210 are syringe-type members that pricks the user's skin and simultaneously draws the fluid to the reagent material 152,252 for analysis. Alternatively, the penetrating members 110,210 of FIGS. 1a-c and 2a-c may also be located adjacent to respective channel 120,220 such that the user only needs to move his/her pricked finger a slight distance to allow the blood to enter the channel 120,220 and be analyzed by the meter. It is contemplated that other types of penetrating members may be used to prick the user's skin and draw the fluid. Some non-limiting examples of the penetrating member may include, but are not limited to, a sharp point, a lance, a hollow point needle, a syringe, a needle, a pin, or other penetrating device. It is contemplated that the penetrating members 110,210 may be used to prick other areas besides a finger such as alternative sites including, but not limited to the arms or legs.

Referring to FIGS. 3a, 3b, test sensors 300a, 300b are shown. In one embodiment, test sensors 300a, 300b include a respective penetrating member 310, a base 312, a spacer 314, and a lid 316, similar to the test sensor 100 previously described. It is contemplated that the test sensors 300a, 300b may be formed without the spacer 314, similar to the test sensor 200 previously described.

According to one embodiment, a plurality of test sensors 300 is removably connected with each other. One non-limiting example of the plurality of test sensors being removably connected is depicted in FIGS. 3a-c. Referring to FIG. 3c, a second opposing end 362a of the test sensor 300a is removably connected to a first opposing end 360b of the adjacent test sensor 300b. Similarly, a second opposing end 362b of the test sensor 300b is removably connected to a first opposing end 360c of the adjacent test sensor 300c having a second opposing end 362c and a base 316c. The adjacent test sensors 300a, 300b, 300c may be removably connected along a perforated contour 370. The perforated connection is desirably configured so that the test sensors may be separated with relatively little force, but still enough connectivity to remain together when no force is being applied. It is also contemplated that other types of removable connections may be used to connect a plurality of test sensors. A few non-limiting examples include a line of weakness, a perforated connection, a pre-cut connection, a glue connection, a welded connection, a perforation, or a tongue and groove connection.

In another embodiment, the plurality of test sensors is removably connected as described above, as well as also being attached to a continuous strip of sealing tape 330, shown in FIG. 3b. In this embodiment, the sealing tape 330 protects a reagent material 352 from contaminates in the environment. The sealing tape 330 may also protect a user from an accidental pricking from the penetrating member 310. It is also contemplated that the sealing tape 330 may be attached to either the base 312 or the lid 316 of the plurality of test sensors 300. Alternatively, it is contemplated that the sealing tape 330 may be placed on both the base 312 and the lid 316 of the plurality of sensors 300.

In another embodiment, the plurality of test sensors is not directly connected to each other. In this embodiment, the plurality of test sensors is closely located on a continuous strip such that the strip maintains a slight separation of the test sensors. One non-limiting example of such a continuous strip is a sealing tape strip (e.g., the sealing strip 330 of FIG. 3b). The sealing tape acts to hold the relative positions of the test sensors such that when the sealing tape moves, all of the attached plurality of test sensors moves accordingly.

In another embodiment, the test sensors may be optical test sensors. Optical test sensor systems may use techniques such as, for example, transmission spectroscopy, diffuse reflectance, or fluorescence spectroscopy for measuring information relating to the fluid analyte such as, for example, the analyte concentration. An indicator reagent system and an analyte in a sample of body fluid are reacted to produce a chromatic reaction, as the reaction between the reagent and analyte causes the sample to change color. The degree of color change is indicative of the analyte concentration in the body fluid. The color change of the sample is evaluated to measure the absorbance level of the transmitted light.

The optical test sensors may be generally similar to test sensors 100, 200, and 300 described above. The optical test sensors may include a penetrating member, a reagent material, a base, a spacer, and a lid. Alternatively, the optical test sensor may include a penetrating member, a reagent material, a base, and a lid. The optical test sensors, however, would not need to include electrodes, conductive leads, or test-sensor contacts.

Figure 4B:
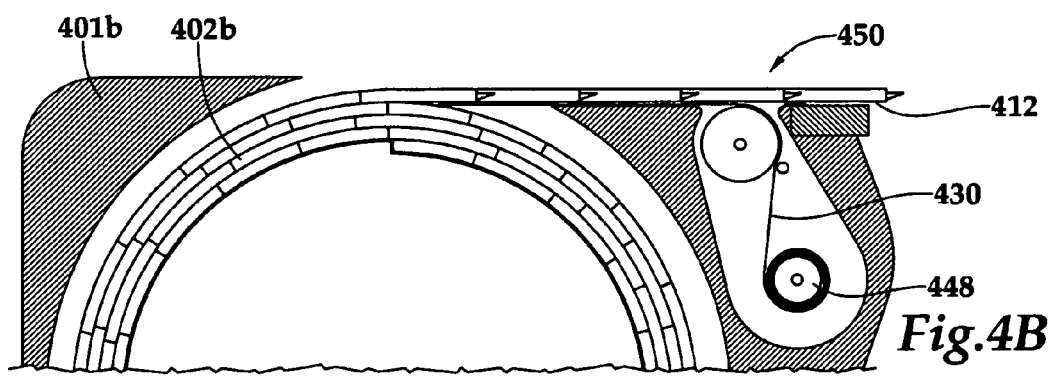
FIG. 4b is a front view of a meter with the housing cut-away according to another embodiment.

Referring to FIGS. 4a and 4b, two different embodiments of the present invention are shown. Each of these embodiments illustrates a meter 400, 450 employing a different method of separating and storing the sealing tape 430 from the plurality of test sensors 402a,b. FIG. 4a illustrates a method of using a plurality of rollers 440, 442, and 444 to separate the sealing tape 430 from the plurality of test sensors 402a and place the sealing tape 430 into a holding area 446. FIG. 4b illustrates another method of separating and storing the sealing tape 430 by winding the sealing tape 430 around a roller 448. In both of these illustrative embodiments, a user desirably accesses and removes the discarded sealing tape 430 from a meter housing 401a, 401b.

Figure 4C:
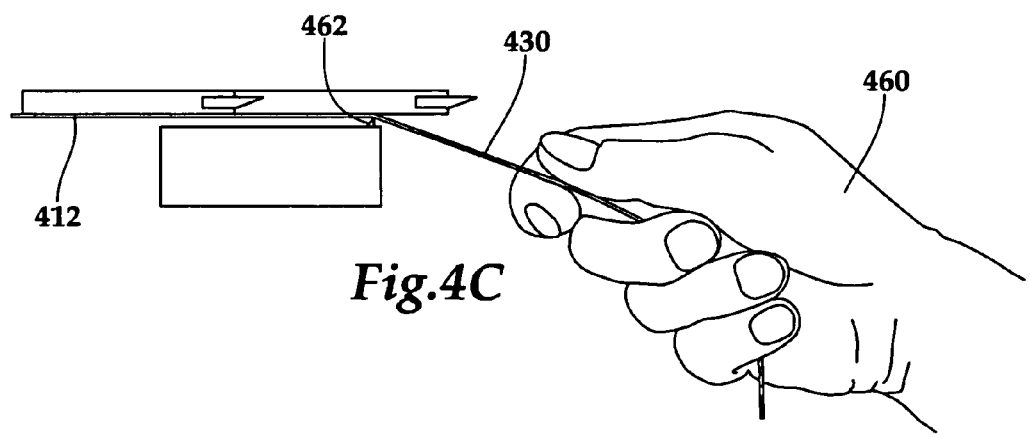
FIG. 4c is a front view of a portion of a meter according to another embodiment.

Referring to FIG. 4c, a further method of separating the sealing tape 430 is shown. FIG. 4c depicts a user 460 manually pulling on the sealing tape 430 to engage the sealing tape 430 against a cutting edge 462. The cutting edge 462 desirably includes a sharp tip to assist in breaking off the sealing tape 430. In all three of the illustrative embodiments shown in FIGS. 4a-c, the sealing tape 430 is shown only attached to a base 412 of the plurality of test sensors 402. It is contemplated that the sealing tape 430 may also be attached to a respective lid 416 of the plurality of test sensors 402.

Referring to FIG. 5a, an integrated meter system 500 is shown according to one embodiment. The integrated meter system 500 includes a display 502, at least one input mechanism 504, a memory device 506, a processor 508, a test-sensor advancement mechanism 520, and a plurality of test sensors 510. The display 502 is adapted to display information to a user. The information typically displayed includes concentration readings, time and date indicators, markers, alarms, logbooks, etc., and any combination of such items. The at least one user input mechanism 504 is adapted to allow the user to make selections relating to one or more user features. The user input mechanism may include, for example, buttons, scroll bars, touch screens, or any combination of such items. The memory device 506 is adapted to store concentration readings. The processor 508 is coupled to the display 502 and adapted to assist in displaying the concentration readings. In some embodiments, the processor 508 may also include a memory. The integrated meter system 500 may also include a software program for providing certain user features.

The display 502 may include any of several types of displays for a graphical user interface. For example, the display 502 may include an LCD display, a graphics display, a plasma display, a backlit display, a combination segmented/graphic display or any other suitable display. In certain embodiments, the integrated meter system 500 may not include a display, but instead provide a printout of the concentration readings. In these embodiments, the results of the measurement can be communicated to the user by an audible sound or by a vibration.

In another non-limiting embodiment, the processor 508 may be adapted to transmit information to other devices that can be used to display a concentration reading. The processor 508 may also be adapted to receive information from other devices, such as a PDA device for example, that can be used to display the concentration reading. The software program that is included in the integrated meter system may be written in any programming language that is typically used in computers, such as Visual Basic, Java, HTML, etc., as well as spreadsheet-application programs such as Microsoft Excel®.

Figure 5C:
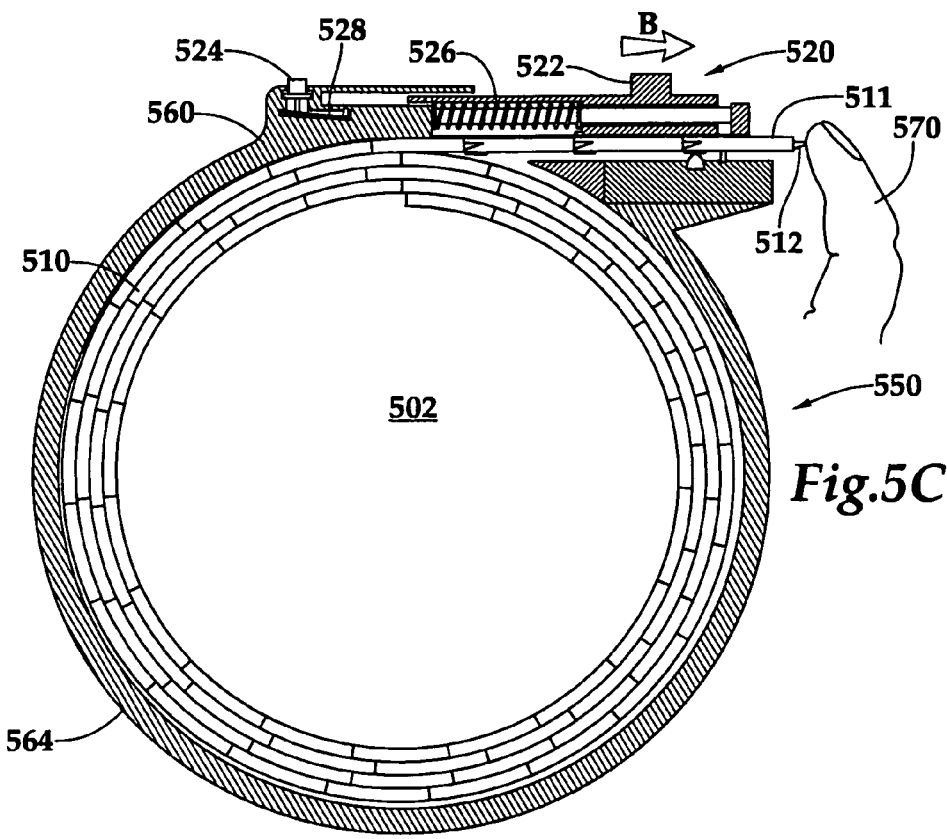
FIG. 5c is a front view of the meter with the housing cut-away shown in FIG. 5b with the leading test-sensor extended in the sampling position according to one embodiment.

Referring to FIGS. 5b and 5c, an integrated meter system 550 is shown in two different positions according to one embodiment, with the housing cut-away. The integrated meter system 550 includes a plurality of test sensors 510, a test sensor-advancement mechanism 520, and a housing 560.

The test sensor-advancement mechanism 520 is used to assist in advancing the plurality of test sensors 510. The test sensor-advancement mechanism 520 includes a plunger 522 and a release button 524. The plunger 522 is attached to the housing 560 such that the plunger 522 may engage at least one of the plurality of test sensors 510. It is contemplated that the plunger 522 may be removably connected to the housing 560.

The plunger 522 has at least two positions: a loaded position and a sampling position. In one method, a user must first move or cock the plunger 522 (in the direction of arrow A of FIG. 5b) to engage the plunger 522 with the release button 524, which places the plunger 522 in the loaded position, as shown in FIG. 5b. The release button 524 maintains contact with a plunger-engagement member 528. The plunger-engagement member 528 has two opposing ends. One of the opposing ends engages the plunger and the other opposing end contacts the release button 524. The plunger 522 may be spring loaded in which a spring 526 supplies the necessary force to drive a penetrating member 512, of a leading test sensor 511, into the skin of a user 570.

According to one method, a user activates (e.g., presses) the release button 524, which causes the plunger-engagement member 528 to disengage the plunger. Once the plunger is disengaged, the leading test sensor 511 is advanced, followed by the same incremental advancement of all the remaining plurality of test sensors 510. After the release button 524 is activated, the plunger 522 is moved in the direction of arrow B in FIG. 5c. The advancement of the leading test sensor 511 forces the integrated penetrating member 512 to pierce the skin of the user placing the plunger 522 in the sampling position, as shown in FIG. 5c. The integrated meter system 550 then processes the fluid sample and may display the information related to the analyte of the fluid sample to the user on the display, if supplied.

It is contemplated other test sensor-advancement mechanisms may be used to advance the plurality of test sensors 510 including, but not limited to, a motor-advancement system, a gear-advancement system, a belt-advancement system, and a ratchet-advancement system.

It is also contemplated that the plunger 522 has a third position such as a standby position, in which the plunger 522 is not engaged by the release button 524 and the test sensor is not engaged by the plunger 522. It is contemplated that the housing contains a top portion 562 (shown in FIG. 5a) and a bottom portion 564 (shown in FIGS. 5b,c), the top portion 562 being connected to the bottom portion 564. Some non-limiting examples of the housing connection include, but are not limited to, a pivoting connection, a glue connection, a hinge connection, a snap connection, a magnetic connection, a screw connection, or a thread/twist connection. The removably connected top and bottom portions 562, 564 allow a user to easily insert the plurality of test sensors 510, or a cartridge of test sensors 670 into the meter 500, 550, 600.

Figure 6:
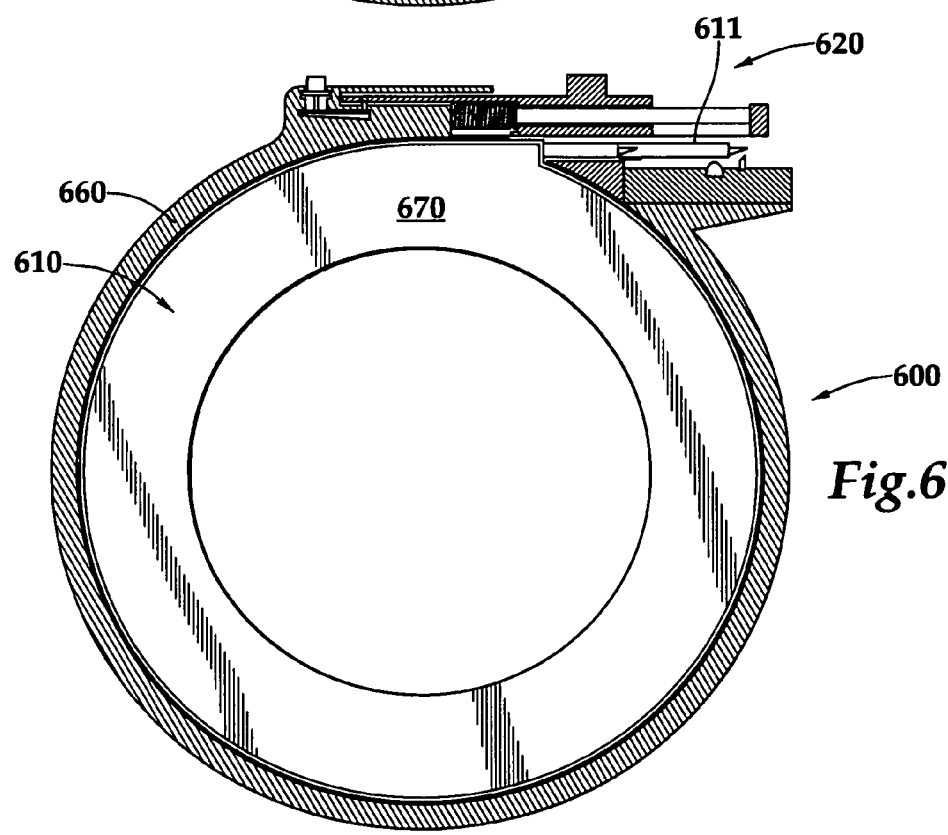
FIG. 6 is a front view of a meter with the housing cut-away including a cartridge according to one embodiment of the present invention.

Referring to FIG. 6, an integrated meter system 600 is shown according to one embodiment, with the housing cut-away. The integrated meter system 600 includes a plurality of test sensors 610, a test sensor-advancement mechanism 620, a housing 660, and a cartridge 670. The plurality of test sensors 610 is located inside the cartridge 670. The cartridge contains at least one opening to allow a user to pull out a leading test sensor 611 such that the plurality of removably connected test sensors 610 is incrementally advanced. The cartridge 670 is removably located into the housing 660 such that the test sensor-advancement mechanism 620 may engage the leading test sensor 611 and incrementally advance the plurality of test sensors 610 from the cartridge 670 as needed. It is contemplated that the cartridge may be supplied in different shapes and sizes including, but not limited to, circular, rectangular, square, triangular, hexagonal, any polygonal shape, etc.

Figure 7A:
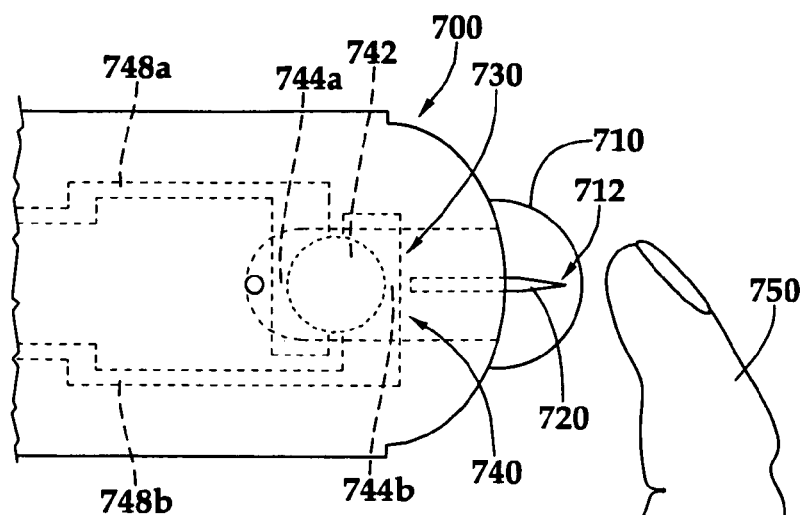
FIG. 7a is a top view of a test sensor with a sealing member attached thereto according to one embodiment.

Referring to FIG. 7a, another embodiment of the present invention is shown. FIG. 7a depicts a test sensor 700 including a sealing member 710, a penetrating member 720, a channel 730, and a testing portion 740. The testing portion 740 is the same or similar to the testing portion 150 described above and shown in FIG. 1c. The testing portion 740 includes a reagent material 742 and at least two electrodes 744a,b. The at least two electrodes 744a,b are electrically connected to contacts via conductive leads 748a and 748b.

The sealing member 710 protects the penetrating member 720 and the channel 730 from contamination in the atmosphere and environment, as well as, protects the reagent material 742 from humidity, oxygen, and other contaminates. Specifically, the sealing member 710 encloses the fluid-receiving area 712 and the penetrating member 720. The fluid receiving area 712 may be adjacent to or within the penetrating member 720. The sealing member 710 may be made of a polymeric material such as polycarbonate, polyethylene terephthalate (PET), polyethylene naphthalate (PEN), polyimide, and combinations thereof. It is contemplated that other materials may be used to form the sealing member.

Figure 7B:
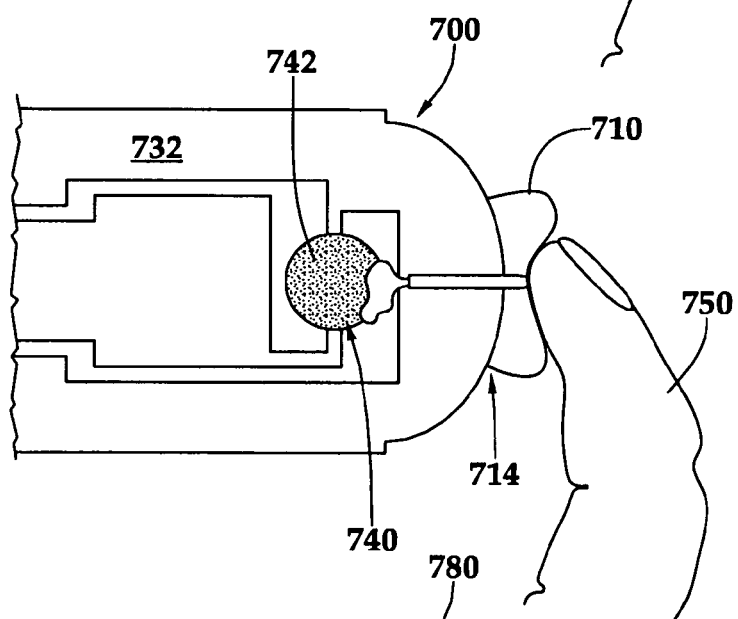
FIG. 7b is a top view of the test sensor of FIG. 7a with the sealing member deformed and in the sampling position.

FIG. 7b depicts one embodiment of the present invention, in which the test sensor 700 of FIG. 7a is in the sampling position. In this embodiment, a user first loads the test sensor 700 in an integrated meter system for testing. A test sensor-advancement mechanism engages the test sensor 700 and causes the sealing member 710 to press against a user's finger 750. The sealing member 710 deforms under the compression between the user's finger 750 and the test sensor 700 such that the penetrating member 720 pierces the sealing member 710 and also breaks the skin of the user's finger, as shown in FIG. 7b.

It is contemplated that the sealing member 710 may be formed of shapes other than that depicted in FIGS. 7a,7b. It is also contemplated that the sealing member 710 may be a separate member adapted to mate with a first end 714 of the test sensor 700. (See FIG. 7b). It is further contemplated that the sealing member 710 may be physically integrated with the test sensor 700 such that material of the test sensor's base 732 and lid are used to form the sealing member 710. It is also contemplated that any portion of the user's skin may be pierced by the penetrating member 720 by this method.

It is further contemplated that the penetrating member 720 is a syringe-type member that draws the blood of the user directly into the channel 730 and to the testing portion 740. Yet in certain other embodiments, the penetrating member 720 pierces the skin of the user and the user applies a sample of blood to an adjacent area of the test sensor 700 for testing. It is contemplated that the penetrating member 720 may also pierce the skin of a user such that blood flows into the sealing member 710 and to the testing portion 740 through the channel 730 without the user having to apply the blood to an adjacent area of the test sensor 700.

Figure 7C:
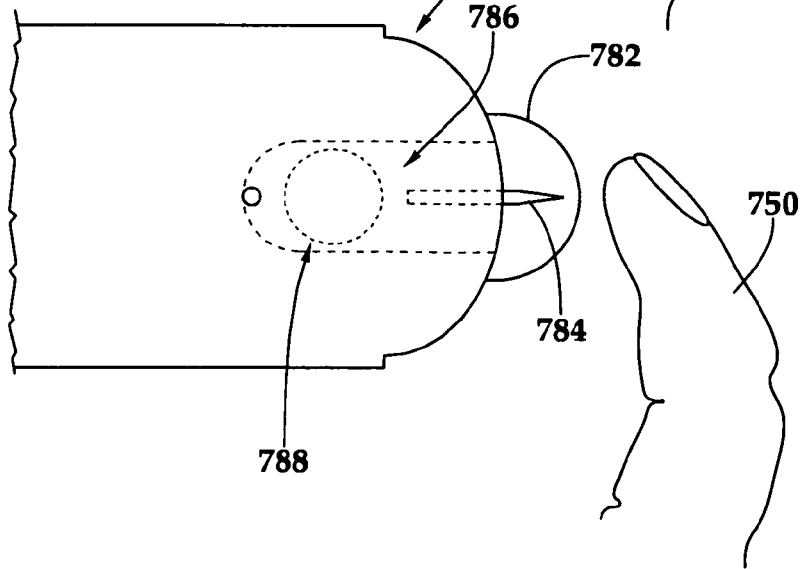
FIG. 7c is a top view of a test sensor with a sealing member attached thereto according to another embodiment of the present invention.

Referring to FIG. 7c, another non-limiting embodiment of the present invention is shown. The test sensor 780 is an optical test sensor. The test sensor 780 includes a sealing member 782, a penetrating member 784, a channel 786, and a testing portion 788. The test sensor 780 may be used with an integrated meter system in a similar manner as the test sensor 700 described above.

Referring to FIGS. 8a and 8b, another non-limiting embodiment of the present invention is shown. FIGS. 8a,b depict an electrochemical test sensor 800 including a penetrating member 810, a base 812, a spacer 814, a lid 816, and a test portion 850. To form the test sensor 800, the base 812, the spacer 814, and the lid 816 are attached by, for example, an adhesive or heat sealing. A channel 820 (e.g., capillary channel) is formed when the base 812, the spacer 814, and the lid 816 are attached to each other.

The penetrating member 810 is slidably engaged to the lid 816. The lid 816 forms a notch 860 thereon to allow a penetrating-member advancement mechanism 870 to engage the penetrating member 810 such that the penetrating-member advancement mechanism 870 slides or pushes the penetrating member 810 in the direction of arrow A shown in FIGS. 8c,d. The penetrating-member advancement mechanism 870 engages the penetrating member 810 and slides or pushes the penetrating member with respect to test sensor 800.

FIG. 8b depicts the testing portion 850 including at least two electrodes 830 and 832 and a reagent material 852. The testing portion 850 may be the same or similar to the testing portion 150 described above in relation to the test sensor 100.

It is contemplated that the penetrating member 810 may pierce a sealing member (e.g., sealing members 710, 782 of FIGS. 7a-c) attached to test sensor 800 as the penetrating member 810 slides in the direction of arrow A. The sealing member may be used to protect the penetrating member 810 and the reagent material 852 from contaminates in the environment, humidity, and oxygen. It is also contemplated that the penetrating member 810 may be a syringe-type member that draws the blood of the user directly to the testing portion 850. It is contemplated that test sensor 800 may also be configured as an optical test sensor, similar to test sensor 780 described above. It is also contemplated that test sensor 800 may be configured without the spacer 814 in a similar manner as test sensor 200 described above.

It is contemplated that all of the above described integrated meter systems may be used with a single stand-alone test sensor integrated with a penetrating member. The integrated meter systems may also be used with a continuous connected plurality of test sensors, with an integrated penetrating member, the plurality of test sensors either being placed directly into a housing or in a cartridge, in which the cartridge is placed into the housing.

Alternate Embodiment A

An integrated meter system for determining information related to an analyte of a fluid sample, the integrated meter system comprising:
  a meter including a housing;
  a plurality of test sensors, each of the plurality of test sensors including a penetrating member, a testing portion, and a channel, the channel being adapted to receive the fluid sample, the plurality of test sensors being removably located within the housing, at least one of the plurality of test sensors being removably connected to an adjacent test sensor; and
  a test-sensor advancement mechanism configured to advance the plurality of test sensors.

Alternate Embodiment B

The integrated meter system of alternate embodiment A, further comprising:
  a display adapted to convey information related to the analyte of the fluid sample; and
  a processor adapted to assist in processing information related to the analyte of the fluid sample, the processor being coupled to the display.

Alternate Embodiment C

The integrated meter system of alternate embodiment A, further comprising a cartridge, the cartridge enclosing the plurality of test sensors, the cartridge being removably located within the housing.

Alternate Embodiment D

The integrated meter system of alternate embodiment A, wherein each one of the plurality of test sensors includes a first opposing end and a second opposing end, the first opposing end of at least one of the plurality of test sensors being removably connected to the second opposing end of an adjacent test sensor.

Alternate Embodiment E

The integrated meter system of alternate embodiment D, wherein the channel is adjacent to the penetrating member, the channel and the penetrating member being located on the first opposing end of each of the plurality of test sensors.

Alternate Embodiment F

The integrated meter system of alternate embodiment D, wherein the first opposing end of at least one of the test sensors is removably connected to the second opposing end of an adjacent test sensor along a perforation.

Alternate Embodiment G

The integrated meter system of alternate embodiment A, wherein the housing has a top portion and a bottom portion, the top portion being pivotably connected to the bottom portion of the housing.

Alternate Embodiment H

The integrated meter system of alternate embodiment A, wherein the test-sensor advancement mechanism includes a spring-loaded plunger and a release button.

Alternate Embodiment I

The integrated meter system of alternate embodiment I, wherein the spring-loaded plunger has a loaded position and a sampling position.

Alternate Embodiment J

The integrated meter system of alternate embodiment A, wherein the penetrating member includes a sharp point, a lance, a hollow point needle, a syringe, a needle, or a pin.

Alternate Embodiment K

The integrated meter system of alternate embodiment A, further comprising a sealing member, the sealing member enclosing the penetrating member and the channel and assisting in preventing or inhibiting communication with the atmosphere.

Alternate Embodiment L

A method of forming a test sensor system adapted to assist in determining information related to an analyte of a fluid sample, the test-sensor system including:

providing a plurality of test sensors, each of the test sensors including a base, a second layer attached to the base and assisting in forming a channel therein to receive the fluid sample, reagent material located within the channel, and a penetrating member, the penetrating member being attached at least to the base or the second layer; and attaching a sealing tape to a surface of each of the plurality of test sensors to assist in preventing or inhibiting communication between the reagent material and the atmosphere.

Alternate Embodiment M

The method of alternate embodiment L, wherein each of the plurality of test sensors are removably connected with each other via a perforation.

Alternate Embodiment N

The method of alternate embodiment L, wherein each of the plurality of test sensors are connected with each other by only the sealing tape.

Alternate Embodiment O

A method of using an integrated meter system for determining information related to an analyte of a fluid sample, the method comprising the acts of:

providing a meter, the meter including a housing;

providing a plurality of test sensors, at least one of the plurality of test sensors being removably connected to an adjacent test sensor, each one of the plurality of test sensors including a penetrating member, a testing portion, and a channel, the channel being adapted to receive the fluid sample and in communication with the testing portion, the plurality of test sensors located within the housing;

advancing at least one of the plurality of test sensors incrementally;

engaging the penetrating member of one of the plurality of test sensors with a portion of a user's skin;

collecting the fluid sample through the channel to the testing portion; and determining the information related to the analyte of the fluid sample.

Alternate Embodiment P

The method of alternate embodiment O, wherein the meter further includes a release button and a spring-loaded plunger and wherein the advancing at least one of the plurality of test sensors incrementally includes pressing the release button to disengage the spring-loaded plunger resulting in incrementally advancing the plurality of test sensors.

Alternate Embodiment Q

An integrated meter system for determining information related to an analyte of a fluid sample, the integrated meter system comprising:

a meter including a housing;

a plurality of test sensors, each of the plurality of test sensors including a lid, a base, a penetrating member, a testing portion, and a channel, the channel being adapted to receive the fluid sample, the plurality of test sensors being removably located within the housing, at least one of the plurality of test sensors being removably connected to an adjacent test sensor;

a sealing member being removably connected to at least one of the respective lids and/or bases of the plurality of test sensors; and a test-sensor advancement mechanism configured to advance the plurality of test sensors.

Alternate Embodiment R

The integrated meter system of alternate embodiment Q, further comprising a cartridge enclosing the plurality of test sensors, the cartridge being removably located within the housing.

Alternate Embodiment S

The integrated meter system of alternate embodiment Q, wherein the test-sensor advancement mechanism includes a spring-loaded plunger and a release button.

Alternate Embodiment T

The integrated meter system of alternate embodiment Q, wherein the sealing member encloses the penetrating member and the channel, and assists in preventing or inhibiting communication with the atmosphere.

Alternate Embodiment U

The integrated meter system of alternate embodiment Q, wherein the sealing member is a sealing tape.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents, and alternatives falling within the spirit and scope of the invention.

What is claimed is:

1. An integrated meter system, comprising:

a meter housing;

a plurality of test sensors removably located within the meter housing, each of the plurality of test sensors including a penetrating member, a testing portion, and a channel, the channel being adapted to receive a fluid sample, a first one of the plurality of test sensors being removably connected to an adjacent second one of the plurality of test sensors; and a test-sensor advancement mechanism coupled to the meter housing and being configured to advance the plurality of test sensors.

2. The integrated meter system of claim 1, further comprising:

a display adapted to convey an analyte concentration of the fluid sample; and a processor adapted to assist in processing the analyte concentration of the fluid sample, the processor being coupled to the display.

3. The integrated meter system of claim 1, further comprising a cartridge, the cartridge enclosing the plurality of test sensors, the cartridge being removably located within the meter housing.

4. The integrated meter system of claim 1, wherein each one of the plurality of test sensors includes a first opposing end and a second opposing end, the first opposing end of the adjacent second one of the plurality of test sensors being removably connected to the second opposing end of the first one of the plurality of test sensors.

5. The integrated meter system of claim 4, wherein the channel is in fluid communication with the penetrating member, the channel and the penetrating member being located adjacent to the first opposing end of each respective one of the plurality of test sensors.

6. The integrated meter system of claim 4, wherein the first opposing end of the adjacent second one of the plurality of test sensors is removably connected to the second opposing end of the first one of the plurality of test sensors along a perforation.

7. The integrated meter system of claim 1, wherein the meter housing has a top portion and a bottom portion, the top portion being pivotably connected to the bottom portion of the meter housing.

8. The integrated meter system of claim 1, wherein the test-sensor advancement mechanism includes a spring-loaded plunger and a release button, the spring-loaded plunger being coupled to the meter housing and being configured to engage at least one of the plurality of test sensors therein.

9. The integrated meter system of claim 8, wherein the spring-loaded plunger has a loaded position and a sampling position, the spring-loaded plunger being configured to engage the release button in response to being in the loaded position.

10. The integrated meter system of claim 1, wherein the penetrating member includes a sharp point, a lance, a hollow point needle, a syringe, a needle, a pin, or a combination thereof.

11. The integrated meter system of claim 1, further comprising a sealing member, the sealing member enclosing the penetrating member and the channel and assisting in preventing or inhibiting communication with the atmosphere.

12. A method of forming a test sensor system adapted to assist in determining an analyte concentration of a fluid sample, the method comprising:
providing a plurality of test sensors, each of the test sensors including a base, a second layer attached to the base and assisting in forming a channel therein to receive the fluid sample, reagent material located within the channel, and a penetrating member, the penetrating member being attached at least to the base or the second layer, each of the plurality of test sensors being removably connected with each other via a perforation; and
attaching a sealing tape to a surface of each of the plurality of test sensors to assist in preventing or inhibiting communication between the reagent material and the atmosphere.

13. The method of claim 12, wherein each of the plurality of test sensors is connected with each of the other test sensors by the sealing tape.

14. A method of using an integrated meter system for determining an analyte concentration of a fluid sample, the method comprising:
providing a meter including a housing;
providing a plurality of test sensors positioned within the housing, a first one of the plurality of test sensors being removably connected to an adjacent second one of the plurality of test sensors, each one of the plurality of test sensors including a penetrating member, a testing portion, and a channel, the channel being adapted to receive the fluid sample and being in fluid communication with the testing portion;
advancing each one of the plurality of test sensors incrementally;
engaging the penetrating member of the first one of the plurality of test sensors with a portion of a user's skin;
collecting the fluid sample through the penetrating member;
delivering the collected fluid sample through the channel to the testing portion; and
determining the concentration of the analyte of the fluid sample.

15. The method of claim 14, wherein the meter further includes a release button and a spring-loaded plunger and wherein the advancing of each one of the plurality of test sensors incrementally includes pressing the release button to disengage the spring-loaded plunger resulting in incrementally advancing the plurality of test sensors.

16. An integrated meter system for determining an analyte concentration of a fluid sample, the integrated meter system comprising:
a meter housing;
a plurality of test sensors removably located within the meter housing, each of the plurality of test sensors including a lid, a base, a penetrating member, a testing portion, and a channel, the channel being adapted to receive the fluid sample, a first one of the plurality of test sensors being removably connected to an adjacent second one of the plurality of test sensors;
a sealing member removably connected to the respective lids, respective bases, or both, of each one of the plurality of test sensors; and
a test-sensor advancement mechanism coupled to the meter housing and being configured to advance the plurality of test sensors.

17. The integrated meter system of claim 16, further comprising a cartridge enclosing the plurality of test sensors, the cartridge being removably located within the meter housing.

18. The integrated meter system of claim 16, wherein the test-sensor advancement mechanism includes a spring-loaded plunger and a release button, the spring-loaded plunger being coupled to the meter housing and being configured to engage at least one of the plurality of test sensors therein.

19. The integrated meter system of claim 16, wherein the sealing member encloses the penetrating member and the channel, and assists in preventing or inhibiting communication with the atmosphere.

20. The integrated meter system of claim 16, wherein the sealing member is a sealing tape.

* * * * *